(12) United States Patent
Wu et al.

(10) Patent No.: US 10,959,412 B2
(45) Date of Patent: Mar. 30, 2021

(54) METHOD FOR CREATING AN ANIMAL MODEL HAVING TRAUMATIC OPTICAL NERVE INJURY

(71) Applicant: The Eye Hospital of Wenzhou Medical University, Wenzhou (CN)

(72) Inventors: Wencan Wu, Wenzhou (CN); Kaihui Nan, Wenzhou (CN); Ende Wu, Wenzhou (CN); Yuanyuan Chen, Wenzhou (CN); Jing Zhou, Wenzhou (CN)

(73) Assignee: The Eye Hospital of Wenzhou Medical University, Wenzhou (CN)

( * ) Notice: Subject to any disclaimer, the term of this patent is extended or adjusted under 35 U.S.C. 154(b) by 0 days.

(21) Appl. No.: 16/087,272

(22) PCT Filed: Jul. 24, 2017

(86) PCT No.: PCT/CN2017/094079
§ 371 (c)(1),
(2) Date: Sep. 21, 2018

(87) PCT Pub. No.: WO2019/000522
PCT Pub. Date: Jan. 3, 2019

(65) Prior Publication Data
US 2020/0053989 A1    Feb. 20, 2020

(30) Foreign Application Priority Data
Jun. 28, 2017   (CN) .......................... 201710504420.7

(51) Int. Cl.
*A01K 67/00* (2006.01)
*A61B 1/00* (2006.01)
*A01K 67/027* (2006.01)
*A61B 3/11* (2006.01)
*A61B 6/03* (2006.01)
*A61B 6/00* (2006.01)
*A61D 1/00* (2006.01)
*A61B 5/24* (2021.01)

(52) U.S. Cl.
CPC ............ *A01K 67/027* (2013.01); *A61B 3/112* (2013.01); *A61B 5/24* (2021.01); *A61B 6/032* (2013.01); *A61B 6/508* (2013.01); *A61D 1/00* (2013.01); *A01K 2207/30* (2013.01); *A01K 2227/10* (2013.01); *A01K 2267/03* (2013.01)

(58) Field of Classification Search
CPC .... A01K 67/027; A01K 2207/30; A61B 5/24; A61M 2039/0279
USPC .............................................. 800/9; 600/101
See application file for complete search history.

*Primary Examiner* — Shin Lin Chen
(74) *Attorney, Agent, or Firm* — Christensen, Fonder, Dardi & Herbert PLLC

(57) ABSTRACT

A method for creating an animal model of traumatic optic nerve injury, including fully exposing an internal segment of an optic canal as well as adjacent anterior skull base, posterior ethmoid sinus and lateral sphenoid sinus walls through an ethmoid sinus-sphenoid sinus operation pathway under an endoscope, and impacting different sites of the internal segment of the optic canal with controllable impact force to cause optic nerve injury so as to prepare a controllable and quantifiable TONI bionic elastic injury animal model reflecting contusion to an internal segment of an optic canal in a human TONI clinical injury state. With less intracranial combined injury to the animal, the survival rate is high. Different sites of the optic canal are impacted with quantifiable elastic force for the quantitative and qualitative purposes with respect to the injured parts and the injury degree.

6 Claims, No Drawings

METHOD FOR CREATING AN ANIMAL MODEL HAVING TRAUMATIC OPTICAL NERVE INJURY

PRIORITY CLAIM

The present application is a National Phase entry of PCT Application No. PCT/CN2017/094079, filed Jul. 24, 2017, which claims the benefit of Chinese Patent Application No. 201710504420.7, filed Jun. 28, 2017, which are incorporated herein by reference.

TECHNICAL FIELD

The present invention relates to the technical field of disease animal models, specifically to a method for creating an animal model of traumatic optic nerve injury.

BACKGROUND

The optic nerve is deep and concealed between the eyeball and the brain as passing through the outer wall of the sphenoid sinus. Due to the particularity, complexity and individual differences of anatomical structures, the research on the mechanism of traumatic optic nerve injury (TONI) has been stuck in the hypothesis of "force conduction", that is, after external force acts on the craniofacial part, especially on the tempus at the outer upper part of the superciliary arch, the blunt force is transmitted to the inner rear part along the sphenoid ridge till reaching the root of the sphenoid winglet outside the optic canal, and finally is converged at weak bones such as the top wall of the sphenoid sinus and/or the outer wall of the ethmoid sinus to form "impact" which causes deformation, fracture and translocation of the weak bones around the optic canal, and thereby results in axonal injury of the optic nerve. Nevertheless, specific mechanisms, such as how the external force acts, how the internal tissue structure of the optic nerve responds after the action, and how the optic nerve responds to this stress change, are currently inconclusive. Therefore, preparing a controllable, quantitative and bionic TONI animal model is especially important for exploring TONI pathophysiological mechanism, seeking an effective method for promoting regeneration and repair of optic nerve, and popularizing and applying the method.

Although various optic nerve injury animal models have been established, they are all incapable of representing the real clinical impaired state of TONI, which hinders the research on the pathogenesis and therapeutic strategies of TONI. At present, the following optic nerve injury animal models are prepared mostly: (1) optic nerve transection injury models, wherein all or part of the optic nerve is directly cut off at the intraorbital segment or before the optic chiasm, resulting in complete interruption of axons of all or part of retinal ganglion cells (RGCs); (2) optic nerve clamping compression injury models, wherein, after the intraorbital segment of the optic nerve is exposed, vessel forceps and the like are used for direct clamping or compression; (3) optic nerve traction injury models, wherein, after the intraorbital segment of the optic nerve is exposed, the optic nerve is overstretched in a direction parallel or perpendicular to the optic canal to cause diffuse optic nerve axonal injury; and (4) optic nerve impact injury models. The modeling methods are divided into closed and open methods: (1) A closed method is to fix the head of an animal with a helmet and impact the head of the animal with an acceleration impactor to cause TONI. Such model is relatively consistent with the clinical TONI, but because of the heterogeneity of the animal skull, humerus and optic canal anatomy, as well as differences in location, magnitude and direction of the external force during the closed injury and the like, the success rate of preparation is extremely low, and animals often die of severe craniocerebral injury. (2) An open method is to cut the periorbital skin and soft tissues to expose an optic nerve hole, and to impact the orbital bone near the optic nerve hole with external force to cause optic nerve injury. The externally impacted part of this method is mainly bones on the inner wall of the optic canal at the tip of the orbit, but bones here are very thin, so it is difficult to injury the optic nerve through "force conduction". Even if there is "force conduction", since the optic canal moves in a different direction at the anterior skull base, the open models are also different from the clinical TONI based on analyses on the conduction medium, nature, direction, magnitude and the like of force.

An ideal TONI animal model should satisfy the following characteristics: (1) As approximate as possible to the clinical state of human TONI. The conventional methods of cutting, clamping compression, over-stretching, and impacting on the intraorbital side wall or in front of the optic nerve hole are all different from the clinical state of TONI in respects of location of the force, characteristics of the external force, location and extent of the optic nerve injury and the like. TONI is complicated by closed craniocerebral injury, and is an injury mainly resulted from "deformation" of the skull due to elasticity as the blunt force acting on the tempus at the outer upper part of the superciliary arch is conducted through the temporal bone, and the main injury site is the internal segment of the optic canal, not the intraorbital segment. Therefore, it is necessary to simulate such a clinical state during preparation, which is to adopt external impact force to injure the internal segment of the optic canal. (2) The model should have high injury rate, accurate locating, good controllability, accurate quantitative grading, good stability, good repeatability and low trauma to animals, should avoid or reduce craniocerebral injury as much as possible, and should be low in animal mortality. (3) The optic nerve anatomy of the selected experimental animal is as similar as possible to humans, has certain practical value and is easy to standardize. Rats, rabbits, monkeys, cats and the like used in the prior art are far from humans. Dogs, pigs, sheep and the like, which are well developed in nasal sinus and anterior skull base and have anatomical structures similar to humans, may qualify as ideal experimental animals.

SUMMARY

In order to overcome the deficiencies of the prior art, the present invention provides a method for creating an animal model of traumatic optic nerve injury.

The technical solution adopted by the present invention is a method for creating an animal model of traumatic optic nerve injury comprising the following steps of:

(1) selecting a healthy adult beagle without eye diseases, performing computed tomography (CT) on its head, and saving the scan data;

(2) fully exposing an internal segment of an optic canal of the animal as well as adjacent anterior skull base, posterior ethmoid sinus and lateral sphenoid sinus walls by using an ethmoid sinus-sphenoid sinus operation pathway under an endoscope; and (3) impacting the fully exposed internal segment of the optic canal with controllable impact force to cause optic nerve injury to simulate a clinical TONI injury state, thus obtaining a controllable and quantifiable TONI bionic elastic injury animal model.

The creating method further comprises the following step of regularly performing a relative afferent pupillary defect examination and a visual electrophysiological examination on the obtained TONI bionic elastic injury animal model to inspect retinal functions and integrity of the visual pathway so as to confirm success in modeling.

The adult beagle is an adult male beagle.

The impact force for impacting the fully exposed internal segment of the optic canal is 5-50 N.

The beneficial effects of the present invention are as follows: the present invention provides a method for creating an animal model of traumatic optic nerve injury, in which the internal segment of the optic canal as well as the adjacent anterior skull base, posterior ethmoid sinus and lateral sphenoid sinus walls are fully exposed through an ethmoid sinus-sphenoid sinus operation pathway under an endoscope to simulate a clinical TONI injury state, and different sites of the internal segment of the optic canal are impacted with controllable impact force to cause optic nerve injury so as to prepare a controllable and quantifiable TONI bionic elastic injury animal model, which really reflects contusion to the internal segment of the optic canal in the human TONI clinical injury state. With less intracranial combined injury to the animal, the survival rate is high. Different sites of the optic canal are impacted by adopting quantifiable elastic force for the quantitative and qualitative purposes with respect to the injured parts and the injury degree. Opening the ethmoid sinus-sphenoid sinus pathway makes various subsequent experimental interventions on the entire optic nerve after the model is prepared, including intracanalicular nerve tissue sampling, local administration in the optic nerve sphenoid sinus cavity or intrathecal microinjection of the optic nerve and the like, become simple and easy.

DETAILED DESCRIPTION

The present invention will be further described in combination with specific contents. Earlier endoscopic cadaveric head anatomy studies on beagles prove that the sphenoid sinus is located closely below the posterior ethmoid sinus, and the optic canal is located on the lateral wall of the sphenoid sinus, which is substantially similar to humans. The individual differences in organisms' optic canal, nasal sinus and anterior skull base anatomy are great, and according to the evolutionary principle of animals, the anatomical features of the optic canals of pigs, dogs, sheep and the like may be more complicated and variable. Therefore, for a specific animal, how to pre-evaluate, judge and screen, accurate locating under an endoscope during preparation, full exposure of the optic canal and its adjacent structures are key to the success of the preparation of an TONI bionic model. In recent years, the development of digital navigation surgical systems and their widespread clinical application have made it possible. CT is performed on an animal's orbit and nasal sinus before a model is prepared, then the scan data is transmitted to a digital surgical navigation system workstation, and a three-dimensional anatomical structure of the optic canal and adjacent structures is obtained after high-speed image processing to determine the anatomical characteristics of the animal's nasal sinus, optic canal and adjacent structures; and then, real-time guidance is performed using an infrared locator, part of the ethmoid sinus is excised under an endoscope to open the sphenoid sinus, and the optic canal and adjacent structures are accurately identified and located.

Thus, a beagle is used as an experimental animal, the internal segment of the optic canal as well as adjacent anterior skull base, posterior ethmoid sinus and lateral sphenoid sinus walls are fully exposed under the endoscope through the ethmoid sinus-sphenoid sinus operation pathway with real-time guidance of a digital navigation surgical system to simulate a clinical TONI injury state, and different sites of the internal segment of the optic canal are impacted by adopting a special quantitative ballistic launcher to cause optic nerve injury so as to prepare a controllable and quantifiable TONI bionic elastic injury animal model. Different from the conventional methods of cutting, clamping compression, over-stretching, impacting on the intraorbital side wall and the like, we believe it has the following advantages: (1) contusion to the internal segment of the optic canal in the human TONI clinical state is really reflected; (2) the guidance of the digital navigation surgical system facilitates screening of animals before preparation, and at the same time, the method is operated directly under the navigation-guided endoscope, so the locating is accurate, the preparation success rate is high, and the objective evaluation on animal models is facilitated; (3) with less intracranial combined injury to the animal, the survival rate is high; (4) different sites of the optic canal are impacted by adopting quantifiable elastic force for the quantitative and qualitative purposes with respect to the injured parts and the injury degree; (5) opening of the ethmoid sinus-sphenoid sinus pathway makes various subsequent experimental interventions on the entire optic nerve after the model is prepared, including intracanalicular tissue sampling, local administration in the optic nerve sphenoid sinus cavity or intrathecal microinjection of the optic nerve and the like, become simple and easy.

The method for creating an animal model of traumatic optic nerve injury according to the present invention is as follows:

(1) selecting a healthy adult male beagle without eye diseases, performing CT on the head, saving the scan data and importing the data into a digital navigation surgical system;

(2) getting prepared for a routine ophthalmic surgery, anesthetizing the animal after weighing, covering the head with a surgical towel, and exposing the surgical field for disinfection;

(3) fully exposing the internal segment of the optic canal as well as adjacent anterior skull base, posterior ethmoid sinus and lateral sphenoid sinus walls by using an endoscopic ethmoid sinus-sphenoid sinus operation pathway under an endoscope with real-time guidance of a digital navigation surgical system;

(4) impacting different sites of the internal segment of the optic canal by adopting a customized quantitative ballistic launcher with force of 5-50 N to cause optic nerve injury to simulate a clinical TONI injury state, thus obtaining a controllable and quantifiable TONI bionic elastic injury animal model; and (5) performing conventional nursing after the surgery, and after the animal wakes up, regularly performing a relative afferent pupillary defect (RAPD) examination and a visual electrophysiological examination (including electroretinogram and visual evoked potential examination) to inspect retinal functions and integrity of the visual pathway so as to confirm success in modeling.

Described above are merely preferred embodiments of the present invention, the protection scope of the present invention is not limited to the above embodiments, and all technical solutions under the concept of the present invention fall within the protection scope of the present invention. It is noted that those of ordinary skill in the art may make improvements and modifications without departing from the principle of the present invention, and these improvements and modifications shall fall within the protection scope of the present invention.

The invention claimed is:

1. A method for creating an animal model of traumatic optic nerve injury (TONI), comprising the following steps of:
   (1) selecting a healthy adult beagle without eye diseases, performing computed tomography (CT) on the beagle's head, and saving scan data;
   (2) using an endoscope to open an ethmoid-sinus-to-sphenoid-sinus surgical path and to fully expose an internal segment of an optic canal of the animal, as well as adjacent anterior skull base, posterior ethmoid sinus and lateral sphenoid sinus walls; and
   (3) impacting the fully exposed internal segment of the optic canal with controllable impact force to cause optic nerve injury to simulate a clinical TONI state, thus obtaining a controllable and quantifiable TONI bionic elastic injury animal model that is a bionic elastic injury beagle model.

2. The method for creating an animal model of traumatic optic nerve injury (TONI), according to claim 1, further comprising the following step of regularly performing a relative afferent pupillary defect examination and a visual electrophysiological examination on the obtained TONI bionic elastic injury animal model to inspect retinal functions and integrity of a visual pathway so as to confirm success in modeling.

3. The method for creating an animal model of traumatic optic nerve injury (TONI), according to claim 1, wherein the adult beagle is an adult male beagle.

4. The method for creating an animal model of traumatic optic nerve injury (TONI), according to claim 1, wherein the impact force for impacting the fully exposed internal segment of the optic canal is 5-50 N.

5. The method for creating an animal model of traumatic optic nerve injury according to claim 1, further comprising using the endoscope to excise tissue of the ethmoid sinus to open the sphenoid sinus.

6. The method for creating an animal model of traumatic optic nerve injury according to claim 5, further comprising using an infrared locator to guide the endoscope in real time.

* * * * *